US009668917B2

(12) United States Patent
Gifford, III et al.

(10) Patent No.: US 9,668,917 B2
(45) Date of Patent: *Jun. 6, 2017

(54) DRUG DELIVERY TREATMENT DEVICE

(71) Applicant: Novartis AG, Basel (CH)

(72) Inventors: Hanson S. Gifford, III, Menlo Park, CA (US); Cary J. Reich, Menlo Park, CA (US)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/804,008

(22) Filed: Jul. 20, 2015

(65) Prior Publication Data
US 2015/0320596 A1 Nov. 12, 2015

Related U.S. Application Data

(63) Continuation of application No. 11/624,168, filed on Jan. 17, 2007, now Pat. No. 9,084,662.

(60) Provisional application No. 60/759,835, filed on Jan. 17, 2006, provisional application No. 60/783,632, filed on Mar. 17, 2006, provisional application No. 60/824,552, filed on Sep. 5, 2006.

(51) Int. Cl.
*A61M 39/22* (2006.01)
*A61F 9/00* (2006.01)
*A61F 9/007* (2006.01)
*A61M 31/00* (2006.01)

(52) U.S. Cl.
CPC .......... *A61F 9/0017* (2013.01); *A61F 9/0008* (2013.01); *A61F 9/00781* (2013.01); *A61M 31/00* (2013.01); *A61M 39/22* (2013.01)

(58) Field of Classification Search
CPC .. A61F 9/0017; A61F 9/0008; A61F 9/00781; A61M 39/22; A61M 31/00
See application file for complete search history.

(56) References Cited

U.S. PATENT DOCUMENTS 3,767,759 A 10/1973 Wichterle
3,788,327 A 1/1974 Donowitz et al.
(Continued)

FOREIGN PATENT DOCUMENTS

EP 0 228 185 A1 11/1986
EP 1173124 A1 1/2002
(Continued)

OTHER PUBLICATIONS

Barsky et al. "Evaluation of absorbable gelatin film (Gelfilm) in cyclodialysis clefts" Arch. Ophth. 60(6): 1044-1052,(1958).
(Continued)

*Primary Examiner* — Theodore Stigell
(74) *Attorney, Agent, or Firm* — Fred C. Hernandez; Mintz Levin Cohn Ferris Glovsky and Popeo, P.C.

(57) ABSTRACT

Disclosed are devices and methods for treatment of eye disease. The suprachoroidal space is used as a conduit within which to place a drug delivery device. One such drug delivery device may be a tube, wicking element, bioabsorbable polymer structure, or other configuration of drug delivery substrate. The delivery device may include a port on the proximal end to assist in repeat injection, and may include a reservoir to either collect flow from the aqueous to concentrate it along the length of the device, or act as a repository for injected agent.

8 Claims, 8 Drawing Sheets

(56) References Cited

U.S. PATENT DOCUMENTS

| | | |
|---|---|---|
| 3,915,172 A | 10/1975 | Wichterle et al. |
| 4,037,604 A | 7/1977 | Newkirk |
| 4,402,681 A | 9/1983 | Haas et al. |
| 4,457,757 A | 7/1984 | Molteno |
| 4,521,210 A | 6/1985 | Wong |
| 4,554,918 A | 11/1985 | White |
| 4,604,087 A | 8/1986 | Joseph |
| 4,634,418 A | 1/1987 | Binder |
| 4,722,724 A | 2/1988 | Schocket |
| 4,750,901 A | 6/1988 | Molteno |
| 4,782,820 A | 11/1988 | Woods |
| 4,787,885 A | 11/1988 | Binder |
| 4,826,478 A | 5/1989 | Schocket |
| 4,846,172 A | 7/1989 | Berlin |
| 4,863,457 A | 9/1989 | Lee |
| 4,886,488 A | 12/1989 | White |
| 4,900,300 A | 2/1990 | Lee |
| 4,932,966 A | 6/1990 | Christie et al. |
| 4,946,436 A | 8/1990 | Smith |
| 4,957,505 A | 9/1990 | McDonald |
| 4,968,296 A | 11/1990 | Ritch et al. |
| 5,041,081 A | 8/1991 | Odrich |
| 5,071,408 A | 12/1991 | Ahmed |
| 5,073,163 A | 12/1991 | Lippman |
| 5,092,837 A | 3/1992 | Ritch et al. |
| 5,127,901 A | 7/1992 | Odrich |
| 5,171,213 A | 12/1992 | Price, Jr. |
| 5,178,604 A | 1/1993 | Baerveldt et al. |
| 5,180,362 A | 1/1993 | Worst |
| 5,300,020 A | 4/1994 | L'Esperance, Jr. |
| 5,338,291 A | 8/1994 | Speckman et al. |
| 5,342,370 A | 8/1994 | Simon et al. |
| 5,346,464 A | 9/1994 | Camras |
| 5,370,607 A | 12/1994 | Memmen |
| 5,372,577 A | 12/1994 | Ungerleider |
| 5,397,300 A | 3/1995 | Baerveldt et al. |
| 5,433,701 A | 7/1995 | Rubinstein |
| 5,443,505 A | 8/1995 | Wong et al. |
| 5,454,746 A | 10/1995 | Guegan et al. |
| 5,476,445 A | 12/1995 | Baerveldt et al. |
| 5,558,629 A | 9/1996 | Baerveldt et al. |
| 5,558,630 A | 9/1996 | Fisher |
| 5,569,197 A | 10/1996 | Helmus et al. |
| 5,601,094 A | 2/1997 | Reiss |
| 5,626,558 A | 5/1997 | Suson |
| 5,626,559 A | 5/1997 | Solomon |
| 5,651,782 A | 7/1997 | Simon et al. |
| 5,676,944 A | 10/1997 | Alvarado et al. |
| 5,702,414 A | 12/1997 | Richter et al. |
| 5,704,907 A | 1/1998 | Nordquist et al. |
| 5,713,844 A | 2/1998 | Peyman |
| 5,741,292 A | 4/1998 | Mendius |
| 5,743,868 A | 4/1998 | Brown et al. |
| 5,752,928 A | 5/1998 | de Roulhac et al. |
| 5,807,302 A | 9/1998 | Wandel |
| 5,868,697 A | 2/1999 | Richter et al. |
| 5,882,327 A | 3/1999 | Jacob |
| 5,893,837 A | 4/1999 | Eagles et al. |
| 5,968,058 A | 10/1999 | Richter et al. |
| 6,007,510 A | 12/1999 | Nigam |
| 6,007,511 A | 12/1999 | Prywes |
| 6,019,786 A | 2/2000 | Thompson |
| 6,050,970 A | 4/2000 | Baerveldt |
| 6,077,299 A | 6/2000 | Adelberg et al. |
| 6,102,045 A | 8/2000 | Nordquist et al. |
| 6,142,969 A | 11/2000 | Nigam |
| 6,186,974 B1 | 2/2001 | Allan et al. |
| 6,203,513 B1 | 3/2001 | Yaron et al. |
| 6,221,078 B1 | 4/2001 | Bylsma |
| 6,251,090 B1 | 6/2001 | Avery et al. |
| 6,261,256 B1 | 7/2001 | Ahmed |
| 6,264,668 B1 | 7/2001 | Prywes |
| 6,331,313 B1 | 12/2001 | Wong et al. |
| 6,375,642 B1 | 4/2002 | Grieshaber et al. |
| 6,383,219 B1 | 5/2002 | Telandro et al. |
| 6,443,985 B1 | 9/2002 | Woods |
| 6,450,984 B1 | 9/2002 | Lynch et al. |
| 6,464,724 B1 | 10/2002 | Lynch et al. |
| 6,468,283 B1 | 10/2002 | Richter et al. |
| 6,471,666 B1 | 10/2002 | Odrich |
| 6,471,777 B1 | 10/2002 | Kobayashi et al. |
| 6,508,779 B1 | 1/2003 | Suson |
| 6,510,600 B2 | 1/2003 | Yaron et al. |
| 6,524,275 B1 | 2/2003 | Lynch et al. |
| 6,533,768 B1 | 3/2003 | Hill |
| 6,537,568 B2 | 3/2003 | Olejnik et al. |
| 6,544,208 B2 | 4/2003 | Ethier et al. |
| 6,544,249 B1 | 4/2003 | Yu et al. |
| 6,558,342 B1 | 5/2003 | Yaron et al. |
| 6,589,203 B1 | 7/2003 | Mitrev |
| 6,592,621 B1 | 7/2003 | Domino |
| 6,595,945 B2 | 7/2003 | Brown |
| 6,626,858 B2 | 9/2003 | Lynch et al. |
| 6,638,239 B1 | 10/2003 | Bergheim et al. |
| 6,638,305 B2 | 10/2003 | Laguette |
| 6,648,283 B2 | 11/2003 | Chase et al. |
| 6,666,841 B2 | 12/2003 | Gharib et al. |
| 6,676,607 B2 | 1/2004 | de Juan, Jr. et al. |
| 6,699,210 B2 | 3/2004 | Williams et al. |
| 6,699,211 B2 | 3/2004 | Savage |
| 6,719,750 B2 | 4/2004 | Varner et al. |
| 6,726,664 B2 | 4/2004 | Yaron et al. |
| 6,730,056 B1 | 5/2004 | Ghaem et al. |
| 6,736,791 B1 | 5/2004 | Tu et al. |
| 6,741,666 B1 | 5/2004 | Henry et al. |
| 6,780,164 B2 | 8/2004 | Bergheim et al. |
| 6,783,544 B2 | 8/2004 | Lynch et al. |
| 6,827,699 B2 | 12/2004 | Lynch et al. |
| 6,827,700 B2 | 12/2004 | Lynch et al. |
| 6,881,197 B1 | 4/2005 | Nigam |
| 6,881,198 B2 | 4/2005 | Brown |
| 6,939,298 B2 | 9/2005 | Brown et al. |
| 6,955,656 B2 | 10/2005 | Bergheim et al. |
| 6,962,573 B1 | 11/2005 | Wilcox |
| 6,966,888 B2 | 11/2005 | Cullen et al. |
| 6,969,384 B2 | 11/2005 | de Juan, Jr. et al. |
| 6,981,958 B1 | 1/2006 | Gharib et al. |
| 6,989,007 B2 | 1/2006 | Shadduck |
| 7,041,077 B2 | 5/2006 | Shields |
| 7,090,681 B2 | 8/2006 | Weber et al. |
| 7,094,225 B2 | 8/2006 | Tu et al. |
| 7,097,660 B2 | 8/2006 | Portney |
| 7,135,009 B2 | 11/2006 | Tu et al. |
| 7,160,264 B2 | 1/2007 | Lisk, Jr. et al. |
| 7,163,543 B2 | 1/2007 | Smedley et al. |
| 7,186,232 B1 | 3/2007 | Smedley et al. |
| 7,192,412 B1 | 3/2007 | Zhou et al. |
| 7,195,774 B2 | 3/2007 | Carvalho et al. |
| 7,207,965 B2 | 4/2007 | Simon |
| 7,220,238 B2 | 5/2007 | Lynch et al. |
| 7,273,475 B2 | 9/2007 | Tu et al. |
| 7,291,125 B2 | 11/2007 | Coroneo |
| 7,293,873 B2 | 11/2007 | Dai et al. |
| 7,297,130 B2 | 11/2007 | Bergheim et al. |
| 7,331,984 B2 | 2/2008 | Tu et al. |
| 7,341,599 B1 | 3/2008 | Peyman |
| 7,381,221 B2 | 6/2008 | Lang et al. |
| 7,431,710 B2 | 10/2008 | Tu et al. |
| 7,488,303 B1 | 2/2009 | Haffner et al. |
| 7,563,241 B2 | 7/2009 | Tu et al. |
| 7,708,711 B2 | 5/2010 | Tu et al. |
| 7,857,782 B2 | 12/2010 | Tu et al. |
| 7,867,186 B2 | 1/2011 | Haffner et al. |
| 7,867,205 B2 | 1/2011 | Bergheim et al. |
| 9,084,662 B2 * | 7/2015 | Gifford, III ............ A61F 9/0008 |
| 2001/0025150 A1 | 9/2001 | de Juan et al. |
| 2002/0013546 A1 | 1/2002 | Grieshaber et al. |
| 2002/0013572 A1 | 1/2002 | Berlin |
| 2002/0072673 A1 | 6/2002 | Yamamoto et al. |
| 2002/0111608 A1 | 8/2002 | Baerveldt et al. |
| 2002/0128613 A1 | 9/2002 | Nakayama |
| 2002/0133168 A1 | 9/2002 | Smedley et al. |
| 2002/0143284 A1 | 10/2002 | Tu et al. |
| 2002/0156413 A1 | 10/2002 | Williams et al. |

(56) References Cited

U.S. PATENT DOCUMENTS

| | | |
|---|---|---|
| 2002/0165478 A1 | 11/2002 | Gharib et al. |
| 2002/0177856 A1 | 11/2002 | Richter et al. |
| 2002/0188282 A1 | 12/2002 | Greenberg |
| 2002/0193725 A1 | 12/2002 | Odrich |
| 2003/0028225 A1 | 2/2003 | Chow et al. |
| 2003/0028228 A1 | 2/2003 | Sand |
| 2003/0060752 A1 | 3/2003 | Bergheim et al. |
| 2003/0097151 A1 | 5/2003 | Smedley et al. |
| 2003/0097171 A1 | 5/2003 | Elliott |
| 2003/0135149 A1 | 7/2003 | Cullen et al. |
| 2003/0181848 A1 | 9/2003 | Bergheim et al. |
| 2003/0187384 A1 | 10/2003 | Bergheim et al. |
| 2003/0208163 A1 | 11/2003 | Yaron et al. |
| 2003/0229303 A1 | 12/2003 | Haffner et al. |
| 2003/0236483 A1 | 12/2003 | Ren |
| 2003/0236484 A1 | 12/2003 | Lynch et al. |
| 2004/0015140 A1 | 1/2004 | Shields |
| 2004/0024345 A1 | 2/2004 | Gharib et al. |
| 2004/0073156 A1 | 4/2004 | Brown |
| 2004/0082993 A1 | 4/2004 | Woods |
| 2004/0082995 A1 | 4/2004 | Woods |
| 2004/0088048 A1 | 5/2004 | Richter et al. |
| 2004/0092856 A1 | 5/2004 | Dahan |
| 2004/0102729 A1 | 5/2004 | Haffner et al. |
| 2004/0111050 A1 | 6/2004 | Smedley et al. |
| 2004/0111153 A1 | 6/2004 | Woods et al. |
| 2004/0147870 A1 | 7/2004 | Burns et al. |
| 2004/0148022 A1 | 7/2004 | Eggleston |
| 2004/0169820 A1 | 9/2004 | Dai et al. |
| 2004/0193095 A1 | 9/2004 | Shadduck |
| 2004/0193262 A1 | 9/2004 | Shadduck |
| 2004/0210181 A1 | 10/2004 | Vass et al. |
| 2004/0210185 A1 | 10/2004 | Tu et al. |
| 2004/0216749 A1 | 11/2004 | Tu |
| 2004/0225250 A1 | 11/2004 | Yablonski |
| 2004/0236343 A1 | 11/2004 | Taylor et al. |
| 2004/0237971 A1 | 12/2004 | Radhakrishnan et al. |
| 2004/0249333 A1 | 12/2004 | Bergheim et al. |
| 2004/0254517 A1 | 12/2004 | Quiroz-Mercado et al. |
| 2004/0254519 A1 | 12/2004 | Tu et al. |
| 2004/0254520 A1 | 12/2004 | Porteous et al. |
| 2004/0254521 A1 | 12/2004 | Simon |
| 2004/0260228 A1 | 12/2004 | Lynch et al. |
| 2005/0008673 A1 | 1/2005 | Snyder et al. |
| 2005/0021138 A1 | 1/2005 | Woods |
| 2005/0049578 A1 | 3/2005 | Tu et al. |
| 2005/0060032 A1 | 3/2005 | Magnante et al. |
| 2005/0065534 A1 | 3/2005 | Hohl |
| 2005/0085906 A1 | 4/2005 | Hanna |
| 2005/0090806 A1 | 4/2005 | Lynch et al. |
| 2005/0090807 A1 | 4/2005 | Lynch et al. |
| 2005/0107734 A1 | 5/2005 | Coroneo |
| 2005/0113914 A1 | 5/2005 | Miller et al. |
| 2005/0119601 A9 | 6/2005 | Lynch et al. |
| 2005/0119636 A1 | 6/2005 | Haffner et al. |
| 2005/0119737 A1 | 6/2005 | Bene et al. |
| 2005/0125003 A1 | 6/2005 | Pinchuk et al. |
| 2005/0143817 A1 | 6/2005 | Hunter et al. |
| 2005/0149080 A1 | 7/2005 | Hunter et al. |
| 2005/0171507 A1 | 8/2005 | Christian et al. |
| 2005/0175663 A1 | 8/2005 | Hunter et al. |
| 2005/0181011 A1 | 8/2005 | Hunter et al. |
| 2005/0181018 A1 | 8/2005 | Peyman |
| 2005/0181977 A1 | 8/2005 | Hunter et al. |
| 2005/0182350 A1 | 8/2005 | Nigam |
| 2005/0191331 A1 | 9/2005 | Hunter et al. |
| 2005/0192527 A1 | 9/2005 | Gharib et al. |
| 2005/0197613 A1 | 9/2005 | Sniegowski et al. |
| 2005/0209549 A1 | 9/2005 | Bergheim et al. |
| 2005/0209550 A1 | 9/2005 | Bergheim et al. |
| 2005/0232972 A1 | 10/2005 | Odrich |
| 2005/0244462 A1 | 11/2005 | Farooq |
| 2005/0250788 A1 | 11/2005 | Tu et al. |
| 2005/0266047 A1 | 12/2005 | Tu et al. |
| 2005/0267397 A1 | 12/2005 | Bhalla |
| 2005/0267398 A1 | 12/2005 | Protopsaltis et al. |
| 2005/0271704 A1 | 12/2005 | Tu et al. |
| 2005/0273033 A1 | 12/2005 | Grahn et al. |
| 2005/0277864 A1 | 12/2005 | Haffner et al. |
| 2005/0283108 A1 | 12/2005 | Savage |
| 2005/0287188 A1 | 12/2005 | Anderson et al. |
| 2005/0288617 A1 | 12/2005 | Yaron et al. |
| 2005/0288619 A1 | 12/2005 | Gharib et al. |
| 2006/0020248 A1 | 1/2006 | Prescott |
| 2006/0032507 A1 | 2/2006 | Tu |
| 2006/0036207 A1 | 2/2006 | Koonmen et al. |
| 2006/0069340 A1 | 3/2006 | Simon |
| 2006/0074375 A1 | 4/2006 | Bergheim et al. |
| 2006/0084907 A1 | 4/2006 | Bergheim et al. |
| 2006/0116626 A1 | 6/2006 | Smedley et al. |
| 2006/0129215 A1 | 6/2006 | Helmus et al. |
| 2006/0155238 A1 | 7/2006 | Shields |
| 2006/0173397 A1 | 8/2006 | Tu et al. |
| 2006/0195055 A1 | 8/2006 | Bergheim et al. |
| 2006/0195056 A1 | 8/2006 | Bergheim et al. |
| 2006/0200113 A1 | 9/2006 | Haffner et al. |
| 2006/0235367 A1 | 10/2006 | Takashima et al. |
| 2006/0241580 A1 | 10/2006 | Mittelstein et al. |
| 2006/0241749 A1 | 10/2006 | Tu et al. |
| 2006/0259138 A1 | 11/2006 | Peyman |
| 2006/0271186 A1 | 11/2006 | Nishi et al. |
| 2006/0276739 A1 | 12/2006 | Brown |
| 2007/0010827 A1 | 1/2007 | Tu et al. |
| 2007/0088242 A1 | 4/2007 | Coroneo |
| 2007/0088424 A1 | 4/2007 | Greenberg et al. |
| 2007/0088432 A1 | 4/2007 | Solovay et al. |
| 2007/0106235 A1 | 5/2007 | Coroneo |
| 2007/0106236 A1 | 5/2007 | Coroneo |
| 2007/0118147 A1 | 5/2007 | Smedley et al. |
| 2007/0123982 A1 | 5/2007 | Yablonski et al. |
| 2007/0141106 A1 | 6/2007 | Bonutti et al. |
| 2007/0149915 A1 | 6/2007 | Yablonski |
| 2007/0191863 A1 | 8/2007 | De Juan et al. |
| 2007/0207186 A1 | 9/2007 | Scanlon et al. |
| 2007/0208134 A1 | 9/2007 | Hunter et al. |
| 2007/0233037 A1 | 10/2007 | Gifford et al. |
| 2007/0276315 A1 | 11/2007 | Haffner et al. |
| 2007/0276316 A1 | 11/2007 | Haffner et al. |
| 2007/0282244 A1 | 12/2007 | Tu et al. |
| 2007/0282245 A1 | 12/2007 | Tu et al. |
| 2007/0293807 A1 | 12/2007 | Lynch et al. |
| 2008/0015488 A1 | 1/2008 | Tu et al. |
| 2008/0045878 A1 | 2/2008 | Bergheim et al. |
| 2008/0046076 A1 | 2/2008 | Rombach |
| 2008/0097459 A1 | 4/2008 | Kammerlander et al. |
| 2008/0106698 A1 | 5/2008 | Dai et al. |
| 2008/0119864 A1 | 5/2008 | Deinzer et al. |
| 2008/0125862 A1 | 5/2008 | Blake |
| 2008/0129962 A1 | 6/2008 | Dai et al. |
| 2008/0195027 A1 | 8/2008 | Coroneo |
| 2008/0200860 A1 | 8/2008 | Tu et al. |
| 2008/0228127 A1 | 9/2008 | Burns et al. |
| 2008/0234624 A2 | 9/2008 | Bergheim et al. |
| 2009/0036819 A1 | 2/2009 | Tu et al. |
| 2009/0043321 A1 | 2/2009 | Conston et al. |
| 2009/0118702 A1 | 5/2009 | Lazar |
| 2010/0010416 A1 | 1/2010 | Juan, Jr. et al. |
| 2010/0274259 A1 | 10/2010 | Yaron et al. |
| 2011/0028883 A1 | 2/2011 | Juan, Jr. et al. |
| 2011/0098629 A1 | 4/2011 | Juan, Jr. et al. |
| 2011/0238075 A1 | 9/2011 | Clauson et al. |
| 2011/0306915 A1 | 12/2011 | De Juan, Jr. et al. |

FOREIGN PATENT DOCUMENTS

| | | |
|---|---|---|
| EP | 1173125 A1 | 1/2002 |
| EP | 1173126 A1 | 1/2002 |
| EP | 1184010 A2 | 3/2002 |
| EP | 1310222 A2 | 5/2003 |
| EP | 1473004 A2 | 11/2004 |
| EP | 1477146 A2 | 11/2004 |
| EP | 1418868 B1 | 3/2008 |
| EP | 1932492 A1 | 6/2008 |
| EP | 1977724 A1 | 10/2008 |

(56) References Cited

FOREIGN PATENT DOCUMENTS

| | | |
|---|---|---|
| EP | 1545655 B1 | 12/2008 |
| EP | 2027837 A2 | 2/2009 |
| GB | 2101891 A | 1/1983 |
| RU | 2018289 C1 | 8/1994 |
| RU | 2056818 C1 | 3/1996 |
| RU | 2074686 C1 | 3/1997 |
| RU | 2074687 C1 | 3/1997 |
| RU | 2157678 C1 | 10/2000 |
| WO | WO-89/00869 A1 | 2/1989 |
| WO | WO-91/12046 A1 | 8/1991 |
| WO | WO-92/19294 A1 | 11/1992 |
| WO | WO-94/09721 A1 | 5/1994 |
| WO | WO-94/09837 A1 | 5/1994 |
| WO | WO-94/13234 A1 | 6/1994 |
| WO | WO-95/08310 A1 | 3/1995 |
| WO | WO-95/13765 A1 | 5/1995 |
| WO | WO-96/20742 A1 | 7/1996 |
| WO | WO 9620742 A1 * | 7/1996 |
| WO | WO-96/36377 A1 | 11/1996 |
| WO | WO-98/23237 A1 | 6/1998 |
| WO | WO-98/30181 A1 | 7/1998 |
| WO | WO-99/26567 A1 | 6/1999 |
| WO | WO-00/06223 A1 | 2/2000 |
| WO | WO-00/64389 A1 | 11/2000 |
| WO | WO-00/64390 A1 | 11/2000 |
| WO | WO-00/64391 A1 | 11/2000 |
| WO | WO-00/64393 A1 | 11/2000 |
| WO | WO-00/64511 A1 | 11/2000 |
| WO | WO-01/78631 A2 | 10/2001 |
| WO | WO-01/78656 A2 | 10/2001 |
| WO | WO-01/97727 A1 | 12/2001 |
| WO | WO-02/36052 A1 | 5/2002 |
| WO | WO-02/070045 A1 | 9/2002 |
| WO | WO-02/074052 A2 | 9/2002 |
| WO | WO-02/080811 A2 | 10/2002 |
| WO | WO-02/080829 A2 | 10/2002 |
| WO | WO-02/087418 A2 | 11/2002 |
| WO | WO-02/087479 A2 | 11/2002 |
| WO | WO-02/089699 A2 | 11/2002 |
| WO | WO-02/102274 A2 | 12/2002 |
| WO | WO-03/000154 A2 | 1/2003 |
| WO | WO-03/015659 A2 | 2/2003 |
| WO | WO-03/015667 A1 | 2/2003 |
| WO | WO-03/017867 A2 | 3/2003 |
| WO | WO-03/041622 A2 | 5/2003 |
| WO | WO-03/049646 A2 | 6/2003 |
| WO | WO-03/073968 A2 | 9/2003 |
| WO | WO-03/099175 A1 | 12/2003 |
| WO | WO-2004/014218 A2 | 2/2004 |
| WO | WO-2004/026347 A2 | 4/2004 |
| WO | WO-2004/037122 A2 | 5/2004 |
| WO | WO-2004/037127 A2 | 5/2004 |
| WO | WO-2004/043231 A2 | 5/2004 |
| WO | WO-2004/053568 A1 | 6/2004 |
| WO | WO-2004/056294 A1 | 7/2004 |
| WO | WO-2004/060219 A1 | 7/2004 |
| WO | WO-2004/062469 A2 | 7/2004 |
| WO | WO-2004/066871 A2 | 8/2004 |
| WO | WO-2004/073552 A2 | 9/2004 |
| WO | WO-2004/107024 A1 | 12/2004 |
| WO | WO-2004/110391 A2 | 12/2004 |
| WO | WO-2005/016418 A1 | 2/2005 |
| WO | WO-2005/046516 A2 | 5/2005 |
| WO | WO-2005/046516 A1 | 5/2005 |
| WO | WO-2005/055873 A2 | 6/2005 |
| WO | WO-2005/082285 A1 | 9/2005 |
| WO | WO-2005/084587 A2 | 9/2005 |
| WO | WO-2005/105197 A2 | 11/2005 |
| WO | WO-2005/107664 A2 | 11/2005 |
| WO | WO-2005/107845 A1 | 11/2005 |
| WO | WO-2006/012421 A2 | 2/2006 |
| WO | WO-2006/014434 A2 | 2/2006 |
| WO | WO-2006/036715 A2 | 4/2006 |
| WO | WO-2007/084582 | 7/2007 |
| WO | WO-2007/087061 A2 | 8/2007 |
| WO | WO-2007/113832 A2 | 10/2007 |
| WO | WO-2007/115259 A2 | 10/2007 |
| WO | WO-2007/130393 A2 | 11/2007 |
| WO | WO-2008/031231 A1 | 3/2008 |
| WO | WO-2008/061043 A2 | 5/2008 |

OTHER PUBLICATIONS

Bick MW "Use of tantalum for ocular drainage" Arch Ophthal. 42(4): 373-88 (1949).

Bietti "The present state of the use of plastics in eye surgery" Acta Ophthalmol (Copenh) 33(4):337-70 (1955).

Brown et al., "Internal Sclerectomy for Glaucoma Filtering Surgery with an Automated Trephine," Archives of Ophthalmology, 105:133-136 (1987).

Burchfield JC, Kass MA, Wax MB. Primary valve malfunction of the Krupin eye valve with disk. J Glaucoma. Jun. 1997;6(3):152-6.

Chiou et al. "Ultrasound biomicroscopy of eyes undergoing deep sclerectomy with collagen implant" Br J Ophthalmol 80 (1996), pp. 541-544.

Chylack LT, Bellows AR. Molecular sieving in suprachoroidal fluid formation in man. Invest Ophthalmol Vis Sci 17:420, (1978).

Classen et al. "A histopathologic and immunohistorchemical analysis of the filtration bleb after unsuccessful glaucoma seton implantation" Am. J. Ophthalmol. 122:205-12 (1996).

Cohen et al. "First day post-operative review following uncomplicated phacoemulsification" Eye 12(4):634-6 (1998).

Collaborative Normal-Tension Study Group. Comparison of glaucomatous progression between untreated patients with normal-tension glaucoma and patients with therapeutically reduced intraocular pressures. Am J Ophthalmol 1998;126:487-97.

Congdon N, O'Colmain B, Klaver CC, et al. Causes and prevalence of visual impairment among adults in the United States. Arch Ophthalmol 2004;122:477-85.

Demailly et al. "Non-penetrating deep sclerectomy (NPDS) with or without collagen device (CD) in primary open-angle glaucoma: middle-term retrospective study" International Ophthalmology 20: 131-140, 1997.

Derwent English abstract for EP 1184010, published Mar. 6, 2002 entitled: "Drainage unit for an eye, consists of a hollow line, a distribution member, and a pressure relief valve which only allows water to leave the eye chamber above a certain pressure," Accession Nbr. 12409716 [351].

Dinakaran et al. "Is the first post-operative day review necessary following uncomplicated phacoemulsification surgery?" Eye, 14(3A):364-6 (2000).

Draeger "Chirurgische Maβnahmen bei kongenitalem Glaukom" (Surgical Interventions in Congenital Glaucoma) Klin Monatsbl Augenheilkd 1993; 202(5): 425-427 [Article in German with English summary included].

Einmahl, S., et al., "Evaluation of a novel biomaterial in the suprachoroidal space of the rabbit eye," Investigative Opthamology and Visual Sciences, 43:1533-1539, (2002).

Ellis, RA "A Reduction of Intraocular Pressure Using Plastics in Surgery" Am J Ophth. 50; 1960, 733-742.

Emi et al. "Hydrostatic pressure of the suprachoroidal space" Invest. Ophthal. Visual Sci. 30(2):233-238 (1989).

Fanous MM, Cohn RA. Propionibacterium endophthalmitis following Molteno tube repositioning. J Glaucoma. Aug. 1997;6(4):201-2.

Friedman DS, Wolfs RC, O'Colmain BJ, et al. Prevalence of open-angle glaucoma among adults in the United States. Arch Ophthalmol 2004;122:532-8.

Fuchs E. "Detachment of the choroid inadvertently during cataract surgery" [German] von Graefes Arch Ophthalmol, 51:199-224 (1900).

Gills et al. "Action of cyclodlalysis utilizing an implant studied by manometry in a human eye" Exp Eye Res 1967; 6:75-78.

Gills JP "Cyclodialysis implants" South Med J. 1967 60(7):692-5.

Gills, "Cyclodialysis Implants in Human Eyes" Am J Ophth 61:1966,841-846.

(56) References Cited

OTHER PUBLICATIONS

Goldberg "Management of Uncontrolled Glaucoma With the Molteno System" Australian and New Zealand Journal of Ophthalmology 1987; 15: 97-107.
Gordon MO, Kass. MA, for the Ocular Hypertension Treatment Study Group. The Ocular Hypertension Treatment Study. Design and baseline description of the participants. Arch Ophthalmol 1999:573-83.
Grant, W.M. , MD, Further Studies on Facility of Flow Through the Trabecular Meshwork, A.M.A. Archives of Ophthalmololgy, Oct. 1958, vol. 60, pp. 523-533.
Gross et al. "Surgical therapy of chronic glaucoma in aphakia and pseudophakia" Ophthalmology, 95:1195-201 (1988).
Harper SL, Foster CS. Intraocular lens explantation in uveitis. Int Ophthalmol Clin. 2000 Winter; 40(1):107-16.
Harrington "Cataract and Glaucoma. Management of the coexistent conditions and a description of a new operation combining lens extraction with reverse cyclodialysis." Am J Ophthalmol. May, 1966;61(5 Pt 2):1134-40.
Heijl A, Leske MC, Bengtsson B, et al for the Early Manifest Glaucoma Trial Group. Reduction of intraocular pressure and glaucoma progression. Results from the Early Manifest Glaucoma Trial. Arch Ophthalmol 2002;120:1268-79.
Heine I. "Cyclodialysis, a new glaucoma operation" [German] Dtsch Med Wochenschr, 31:824-826 (1905).
Hildebrand et al. "Efficacy of anterior chamber decompression in controlling early intraocular pressure spikes after uneventful phacoemulsification" J. Catact Refract Surg., 29:1087-92 (2003).
Hoskins, et al., "Aqueous Humor Outflow", Becker-Shaffer's Diagnosis and Therapy of the Glaucomas, 6th Edition, Chapter 4, pp. 41-66, 1989.
Howorth D J "Feasibility study for a micromachined glaucoma drainage device" Cranfield University School of industrial and manufacturing science MSc Thesis Academic Year 2001-2002 Sep. 13, 2002.
Hylton, C. and A. Robin et al., "Update on prostaglandin analogs," Current Opinion in Opthamology, 14:65-69, (2003).
Javitt JC, Chiang YP. Preparing for managed competition. Utilization of ambulatory eye care visits to ophthalmologists. Arch Ophthalmol 1993;111:1034-5.
Jay JL, Allan D. The benefit of early trabeculectomy versus conventional management in primary open-angle glaucoma relative to severity of disease. Eye 1989; 3:528-35.
Jordan J. "A Novel Approach to Suprachoroidal Drainage for the Surgical Treatment of Intractable Glaucoma" J. Glaucoma 15:200-205 (2006).
Karlen et al. "Deep sclerectomy with collagen implant: medium term results" Br. J. Ophthalmol, Jan. 1999, 83(1):6-11.
Kass MA, Heuer DK, Higginbotham EJ, et al for the Ocular Hypertension Treatment Study Group. The Ocular HypertensionTreatment Study. A randomized trial determines that topical ocular hypotensive medication delays or prevents the onset of primary open-angle glaucoma. Arch Ophthalmol 2002;120:701-13.
Klemm et al. "Die Ultraschallbiomikroskopie als Kriterium der Funktionsprüfung des suprachorioidalen Spaltes nach kammerwinkelchirurgischen Eingriffen ; (Ultrasound Biomicroscopic Imaging for Assessment of the Suprachoroidal Cleft after Angle Surgery)" Klinische Monatsblätter für Augenheilkunde 1997; 210: 74-77 [Article in German with English summary included].
Klemm et al. "Experimental use of space-retaining substances with extended duration: functional and morphological results" Graefes Arch Clin Exp Ophthalmol Sep. 1995; 233(9):592-7.
Kozlov et al. "Nonpenetrating deep sclerectomy with collagen" Eye microsurgery 3:44-46 (1990) [Russian with English translation].
Krejci "Cyclodialysis with hydroxymethyl methacrylate capillary strip (HCS). Animal experiments with a new approach in glaucoma drainage surgery" Ophthalmologica 1972; 164(2):113-21.
Krejci L. "Microdrainage of anterior chamber of eye glaucoma operation using hydron capillary drain." Acta Univ Carol Med Monogr. 1974;(61):1-90.
Kupfer "Studies on intraocular pressure. I. A technique for polyethylene tube implantation into the anterior chamber of the rabbit." Arch Ophthalmol. Apr. 1961;65:565-70.
La Rocca "Gonioplasty in Glaucoma*A Preliminary Report" Br J Ophth 46:1962, 404-415.
Law et al., "Retinal Complications After Aqueous Shunt Surgical Procedures for Glaucoma" Arch Ophthal.; Dec. 1996; vol. 114:1473-1480.
Lee et al. "Magnetic resonance imaging of the aqueous flow in eyes implanted with the trabeculo-suprachoroidal glaucoma seton" Invest. Ophthalmol. Vis. Sci. 33:948 (1992).
Lee KY. Trabeculo-suprachoroidal shunt for treating recalcitrant and secondary glaucoma. Presented at the American Academy of Ophthalmology Annual Meeting, Anaheim, CA, 1991.
Leske MC, Heijl A, Hussein M, et al for the Early Manifest Glaucoma Trial Group. Factors for glaucoma progression and the effect of treatment. The Early Manifest Glaucoma Trial. Arch Ophthalmol Jan. 2003;121:48-56.
Lichter PR, Musch DC, Gillespie BW, et al and the CIGTS Study Group. Interim clinical outcomes in the Collaborative Initial Glaucoma Treatment Study comparing initial treatment randomized to medications or surgery. Ophthalmology 2001;108:1943-53.
Losche W. "Proposals for improvement of cyclodialysis" Klin Monatsblatter Augenheilkd Augenarztl Fortbild 121(6):715-6 (1952) [German].
Marx et al., "Use of the Ganciclovir Implant in the Treatment of Recurrent Cytomegalovirus Retinitis" Arch Ophthal.; Jul. 1996; vol. 114:815-820.
McPherson "Combined Trabeculotomy and Cataract Extraction as a Single Operation*" Tr. Am. Ophth. Soc., vol. LXXIV, 1976; 251-260.
Mehta KR. "The suprachoroidal hema wedge in glaucoma surgery" American Academy of Ophthalmology meeting 1977 pp. 144.
Migdal C, Gregory W, Hitchings R. Long term functional outcome after early surgery compared with laser and medicine in open-angle glaucoma. Ophthalmology 1994;101:1651-7.
Miglior S, Pfeiffer N, Zeyen T et al for the European Glaucoma Prevention Study Group. Results of the European Glaucoma Prevention Study. Ophthalmology 2005;112:366-75.
Miglior S, Zeyen T, Pfeiffer N, et al for the European Glaucoma Prevention Study Group. The European Glaucoma Prevention Study design and baseline description of the participants. Ophthalmology 2002;109:1612-21.
Miki, MD et al., "Intraocular Cannula for Continuous, Chronic Drug Delivery-Histopathic Observations and Function" Arch Ophthal.; May 1985; vol. 103:712-717.
Molteno et al. "Long tube implants in the management of glaucoma" South African Medical Journal, Jun. 26, 1976;50(27):1062-6.
Molteno et al. "The Vicryl tie technique for inserting a draining implant in the treatment of secondary glaucoma." Australian and New Zealand Journal of Ophthalmology 1986; 14: 343-354.
Moses RA "Detachment of ciliary body-anatomical and physical considerations" Investigative Ophthalmology & Visual Science, Assoc. for Research in Vision and Ophthalmology, US, vol. 4, No. 5, Oct. 1, 1965.
Nesterov AP et al. "Surgical stimulation of the uveoscleral outflow. Experimental studies on enucleated human eyes" Acta Opthalmol (Copenh) June; 57(3):409-17 (1979).
Nguyen et al., "Complications of Baerveldt Glaucoma Drainage Implants" Arch Ophthal.; May 1998; vol. 116:571-575.
O'Brien et al. "Cyclodialysis" Arch Ophthal. 1949;42(5):606-619.
Olsen, Timothy W., et al., Cannulation of the Suprachoroidal Space: A Novel Drug Delivery Methodology to the Posterior Segment, American Journal of Ophthalmology, vol. 142, No. 5, Nov. 2006, pp. 777-787.e2.
Ozdamar et al. "Suprachoroidal seton implantation in refractory glaucoma: a novel surgical technique" J. Glaucoma Aug. 2003; 12(4):354-9.

(56) References Cited

OTHER PUBLICATIONS

Pinnas G. et al. "Cyclodialysis with teflon tube implants" Am J. Ophthalmol 1969 Nove; 68(5):879-883.
Portney GL, "Silicone elastomer implantation cyclodialysis." Arch Ophthalmol 1973; 89: 10-12.
Pruett et al., "The Fishmouth Phenomenon-II. Wedge Scleral Buckling" Arch Ophthal.; Oct. 1977; vol. 95:1782-1787.
Qadeer "Acrylic Gonio-Subconjunctival Plates in Glaucoma Surgery" Br J Ophthalmol. Jun. 1954; 38(6): 353-356.
Quigley HA, Vitale S. Models of open-angle glaucoma prevalence and incidence in the United States. Invest Ophthalmol Vis Sci 1997; 38:83-91.
Richards et al. "Artificial Drainage Tubes for Glaucoma" Am J Ophth 60:1965,405-408.
Ritch, et al., "Uveoscleral Outflow", The Glaucomas. St. Louis: Mosby, 1996; pp. 337-343.
Rosenberg et al. "Implants in glaucoma surgery" Chapter 88, The Glaucomas, Ritch et al. Eds. 2nd Ed. Mosby St. Louis 1986; p. 1783-1807.
Row H. "Operation to control glaucoma: preliminary report" Arch. Ophthal 12:325 (1934).
Rowan, Patrick J., MD, Combined Cyclodialysis and Cataract Surgery, Ophthalmic Surgery and Lasers, Dec. 1998, vol. 29, No. 12, pp. 962-968 (9 pages).
Sampimon "A New Approach to Filtering Glaucoma Surgery" Ophthalmologica (Basel) 151:1966, 637-644.
Schappert S. Office visits for glaucoma: United States, 1991-92. Advance data from vital and health statistics. vol. 262. Hyattsville, MD: National Center for Health Statistics, 1995.
Shaffer RN, Weiss DI. Concerning cyclodialysis and hypotony. Arch Ophthalmol 68: 25, 1962.
SOLX Clinical Literature Handout; Industry Show Feb. 2006; "The SOLX Gold Micro-shunt (GMS) treatment".
Sommer A, Tielsch JM, Katz J, et al. Racial differences in the cause-specific prevalence of blindness in east Baltimore. N. Engl J Med 1991;325:1412-7.
Sourdille et al. "Reticulated hyaluronic acid implant in non-perforating trabecular surgery." J Cataract Refract Surg 25: 332-339. (1999).
Srinivasan et al. "Microbial contamination of the anterior chamber during phacoemulsification" J. Cataract Refract Surg. 28:2173-6 (2002).
Suguro K, Toris CB, Pederson JE. Uveoscleral outflow following cyclodialysis in the monkey eye using a fluorescent tracer. Invest Ophthalmol Vis Sci 1985: 26, 810.
The Advanced Glaucoma Intervention Study (AGIS): 7. The relationship between control of intraocular pressure and visual field deterioration. The AGIS Investigators. Am J Ophthalmol 2000;130:429-40.
The Advanced Glaucoma Intervention Study (AGIS); 13. Comparison of treatment outcomes within race: 10-year results. Ophthalmology 2004;111:651-64.
The Glaucoma Laser Trial (GLT) and Glaucoma Laser Trial Follow-up Study: 7. Results. Am J Ophthahnol 1995;120:718-31.
The Glaucoma Laser Trial (GLT). 2. Results of argon laser trabeculoplasty versus topical medicines. The Glaucoma Laser Trial Research Group. Ophthalmology 1990;97:1403-13.
Tielsch JM, Sommer A, Katz J, et al. Racial variations in the prevalence of primary open-angle glaucoma. The Baltimore Eye Survey. JAMA 1991;266:369-74.
Toris CB. Extravascular albumin concentration of the uvea. Invest Ophthalmol Vis Sci 1990; 31:43.
Toris et al. "Aqueous humor dynamics in the aging human eye" Am J. Ophthalmol., 127:407-12 (1999).
Toris et al. "Effect of intraocular pressure on uveoscleral outflow following cyclodialysis in the monkey eye." Investigative Ophthalmology & Visual Science. 26 (1985) 1745-1749.
Trigler L, Proia AD, Freedman SF. Fibrovascular ingrowth as a cause of Ahmed glaucoma valve failure in children. Am J Ophthalmol. Feb. 2006;141(2):388-9.
Troncosco UM "Cyclodialysis with insertion of metal implant in treatment of glaucoma Preliminary report" Arch. Ophthal. 23:270 (1940).
Troncoso, Manuel U., Tantalum implants for inducing hypotny, Am Journal of Ophthalmology, vol. 32(4):499-508 (1949).
Veen et al. "The gonioseton, a surgical treatment for chronic glaucoma" Documenta Ophthalmologica vol. 75, Nos. 3-4, 365-375. (1990).
Wagner, Justin A., et al., Characterization of Uveoscleral Outflow in Enucleated Porcine Eyes Perfused under Constant Pressure, Invest Ophthalmol Vis Sci., Published in edited form in Sep. 2004, vol. 45, Issue 9, pp. 3203-3206.
Wamsley S, Moster MR, Rai S, Alvim HS, Fontanarosa J. Results of the use of the Ex-Press miniature glaucoma implant in technically challenging, advanced glaucoma cases: a clinical pilot study. Am J Ophthalmol. Dec. 2004; 138(6): 1049-51.
Yablonski, "Some thoughts on the pressure dependence of uveoscleral flow" Journal of Glaucoma, 12(1):90-92 (2003).
Yablonski, "Trabeculectomy with Internal Tube Shunt: a novel glaucoma surgery" J. Glaucoma 14:91-97 (2005).
Zhou et al. "A trabecular bypass flow hypothesis" J Glaucoma. 14(1):74-83 (2005).

* cited by examiner

DRUG DELIVERY TREATMENT DEVICE

RELATED APPLICATIONS

This application is a continuation of U.S. patent application Ser. No. 11/624,168, titled "Drug Delivery Treatment Device," filed Jan. 17, 2007, now U.S. Pat. No. 9,084,662, issued on Jul. 21, 2015, which in turn claims benefit of priority under 35 U.S.C. §119(e) to U.S. Provisional Application Ser. No. 60/759,835, filed Jan. 17, 2006, entitled "GLAUCOMA TREATMENT DEVICE;" to U.S. Provisional Application Ser. No. 60/783,632, filed Mar. 17, 2006, entitled "GLAUCOMA TREATMENT DEVICE"; and to U.S. Provisional Application Ser. No. 60/824,552, filed Sep. 5, 2006, entitled "GLAUCOMA TREATMENT DEVICE."

The subject matter of each of the above-noted applications is hereby incorporated by reference in its entirety.

BACKGROUND

This disclosure relates generally to methods and devices for use in treating various ocular diseases. Glaucoma is caused by a number of different eye diseases which can produce increased intraocular pressure (IOP) in the eye. The increased pressure is often caused by a backup of aqueous humour within the eye. Over time, the increased pressure can cause damage to the optic nerve, which can lead to blindness.

One way to treat glaucoma is to implant a drainage device, or shunt, in the eye. The drainage device functions to drain aqueous humour from the anterior chamber and thereby reduce the intraocular pressure. The drainage device is typically implanted using to an invasive surgical procedure. Pursuant to one such procedure, a flap is surgically formed in the sclera. The flap is folded back to form a small cavity and a shunt is inserted into the eye through the flap. Such a procedure can be quite traumatic for the patient.

The following references describe various devices and procedures for treating glaucoma: U.S. Pat. No. 6,827,700 to Lynch, U.S. Pat. No. 6,666,841 to Bergheim, U.S. Pat. No. 6,508,779 to Suson, U.S. Pat. No. 6,544,208 to Ethier, U.S. Pat. No. 5,601,094 to Reiss, U.S. Pat. No. 6,102,045 to Nordquist, U.S. Patent Application 2002/0156413 to Williams, 2002/0143284 to Tu, 2003/0236483 to Ren, 2002/0193725 to Odrich, 2002/0165478 to Gharib, 2002/0133168 to Smedley, 2005/0107734, 2004/0260228 to Lynch, 2004/0102729 to Haffner, 2004/0015140 to Sheilds, 2004/0254521 to Simon, 2004/0225250 to Yablonski. The aforementioned references are all incorporated herein by reference in their entireties.

Current devices and procedures for treating glaucoma have disadvantages and in some cases only moderate success rates. The procedures are very traumatic to the eye and also require highly accurate surgical skills, such as to properly place the drainage device in a proper location. In addition, the devices that drain fluid from the anterior chamber to a subconjunctival bleb beneath a scleral flap, are prone to infection, and can occlude and cease working. This can require re-operation to remove the device and place another one, or can result in further surgeries. In addition, for agents delivered via direct injection, other complications result, and numerous office visits are required to keep a therapeutic dose resident in the eye. In view of the foregoing, there is a need for improved devices and methods for the treatment of a variety of ocular diseases.

SUMMARY

Disclosed are devices and methods for treatment of eye disease such as glaucoma. Using the devices and introduction and placement techniques of the present invention, it is possible to place a device using the suprachoroidal space as a conduit within which to place a drug delivery device. One such drug delivery device may be a tube, wicking element, bioabsorbable polymer structure, or other configuration of drug delivery substrate. The delivery device may include a port on the proximal end to assist in repeat injection, and may include a reservoir at some point along the device to either collect flow from the aqueous to concentrate it along the length of the device, or act as a repository for injected agent.

In addition, the devices of the present invention may be used to augment and assist delivery of drugs to the back of the eye either through injection into a port of the device, or by directing therapeutic agents placed by drops into the eye, but direction the flow of the aqueous containing the drop, into the suprachoroidal space and beyond, to various locations toward the back of the eye.

Placement of a suprachoroidal implant can also assist in delivering drugs to various locations within the eye, including to the back of the eye.

Injections to the back of the eye to treat a wide variety of systemic and ocular conditions such as inflammation, infection, cancerous growth, may be prevented or treated using the drug delivery devices of the present invention. More specifically, ocular conditions such as glaucoma, proliferative vitreoretinopathy, diabetic retinopathy, dry and wet AMD, uveitis, keratitis, cytomegalovirus retinitis, cystoid macular edema, herpes simplex viral and adenoviral infections can be treated or prevented. In many cases, multiple injections are required, leading to degradation of the injection site, and numerous office visits, resulting in increased cost to the healthcare system as well as issues of compliance with patients.

In one aspect, there is disclosed a device for delivering an agent to the eye, comprising an elongate element adapted for at least partial placement in a suprachoroidal space of the eye, the elongate element having a proximal end and a distal end, wherein the proximal end is positioned at a first location of the eye and wherein the distal end extends to a location within a posterior segment of the eye, the elongate element adapted to deliver a drug into the eye.

In another aspect, there is disclosed a method of delivering drug into the eye, comprising: implanting an elongate element in the eye such that at least a portion of the elongate member is positioned within the suprachoroidal space of the eye, the elongate member adapted to deliver a drug into the eye; and inserting a drug into the elongate member such that the drug flows along the elongate member into the suprachoroidal space.

In another aspect, there is disclosed a method of delivering drug into the eye, comprising: forming an incision in the cornea of the eye; inserting an elongate member through the incision into the eye wherein the elongate member is adapted to transport a drug; passing the delivery device along a pathway through the scleral spur of the eye into the suprachoroidal space; and flowing drug along the delivery device into the suprachoroidal space.

In another aspect, there is disclosed a method of delivering drug into the eye, comprising: implanting an elongate element in the eye such that at least a portion of the elongate member is positioned within the suprachoroidal space of the eye, the elongate member adapted to deliver a drug into the eye; placing a drop of a treatment medium onto the surface of the eye; permitting the treatment medium to flow into the anterior chamber of the eye; and causing the treatment medium to flow into the elongate member such that the treatment medium flows along the elongate member into the suprachoroidal space.

Other features and advantages should be apparent from the following description of various embodiments, which illustrate, by way of example, the principles of the invention.

DETAILED DESCRIPTION

Figure 1:
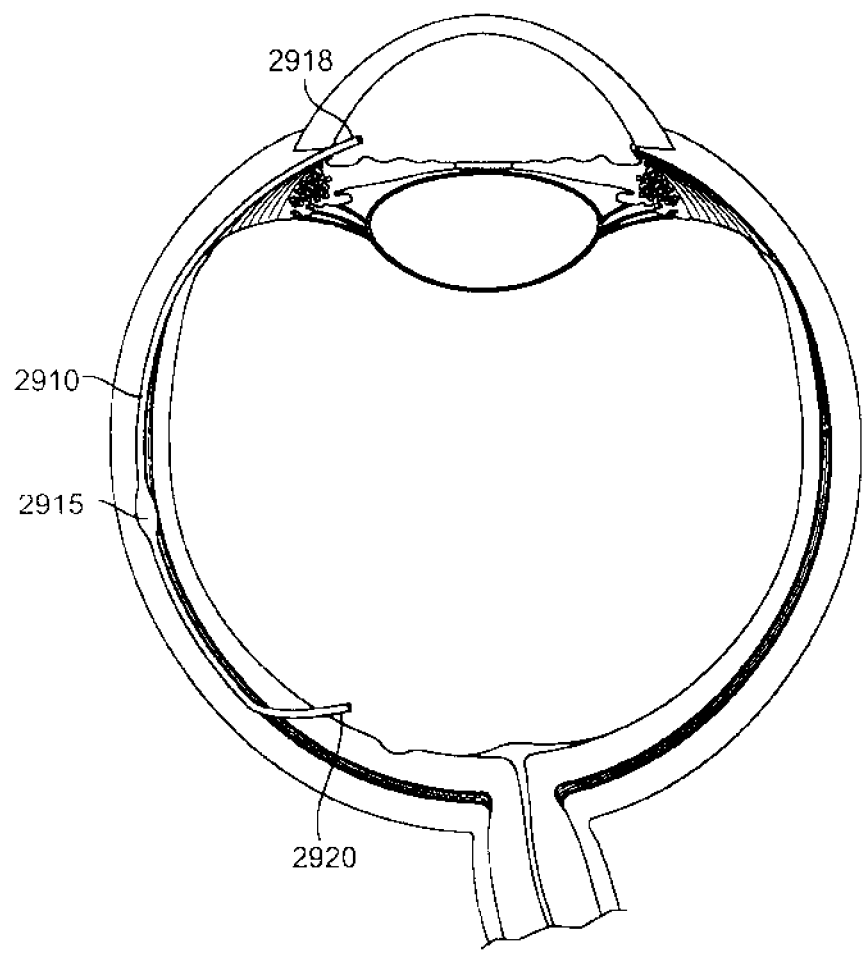
FIG. 1 is a cross-sectional, perspective view of a portion of the eye showing a drug delivery device positioned in the eye.

FIG. 1 is a cross-sectional, perspective view of a portion of the eye showing the anterior and posterior chambers of the eye. A drug delivery device is positioned inside the eye such that a distal end is located in a location of the eye to which one or more drugs are to be delivered. In an exemplary embodiment, the drug delivery device is positioned in the eye such that one or more drugs can be delivered to the suprachoroidal space. Embodiments of the drug delivery device with various structural configurations are described in detail below.

Using the devices and introduction and placement techniques of the present invention, it is possible to place a device that uses the suprachoroidal space as a conduit within which to place a drug delivery device such as the device described herein. One such drug delivery device may be a wicking element, bioabsorbable polymer structure, or other configuration of drug delivery substrate.

FIG. 1 shows an exemplary drug delivery device 2910 extending from a point of entry at the scleral spur, and extending to the back of the eye. At least a portion of the drug delivery device 2910 is positioned within and anchored within the suprachoroidal space and can have a profile that is configured to seal within the suprachoroidal space. Another portion of the drug delivery device 2910 is positioned in a different location of the eye.

One or more drug reservoir regions 2915 may be optionally formed within the suprachoroidal space for receipt of a drug. The drug reservoir region can be a space or volume within the suprachoroidal space into which a drug is inserted. A proximal end or proximal region 2918 of the drug delivery device 2910 can include a port that receives a drug for delivery into the suprachoroidal space, such as into the reservoir region 2915. With the body of the drug delivery device 2910 being anchored within the suprachoroidal space, the distal end and/or the proximal end of the device can be located at various locations relative to the eye to achieve a desired manner of drug delivery, as described below.

Figure 2A:
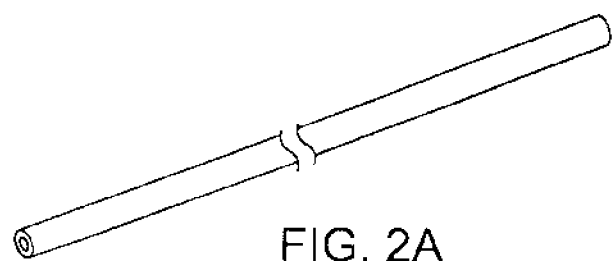
FIG. 2A shows an exemplary embodiment of the drug delivery device.
Figure 2B:
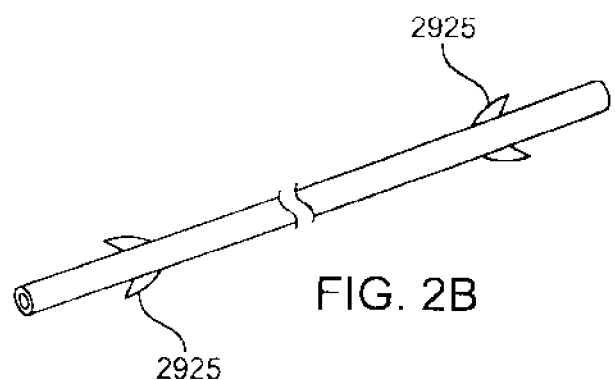
FIG. 2B shows another embodiment of the drug delivery device.
Figure 2C:
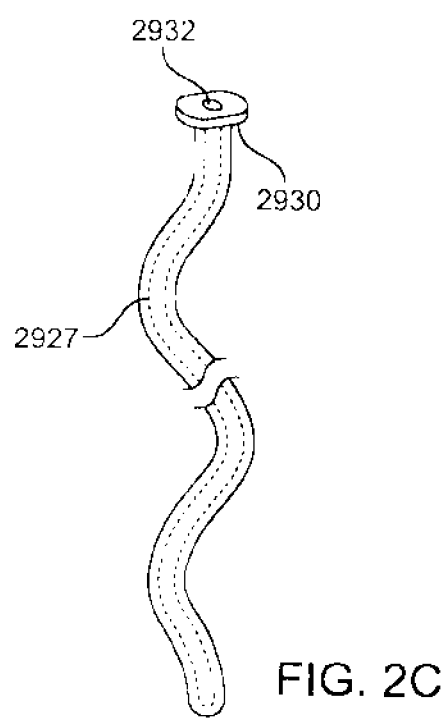
FIG. 2C shows another embodiment of the drug delivery device.

The drug delivery device 2910 can have a variety of structures. For example, as shown in FIG. 2A, the drug delivery device 2910 can be an elongate member with an internal lumen for drug delivery. As shown in FIG. 2B, the drug delivery device 2910 can include one or more retention features, such as prongs 2925, that anchor the drug delivery device in a fixed position within the eye. In another embodiment, shown in FIG. 2C, the drug delivery device 2910 is an elongate member with an internal lumen 2927 and an anchor member, such as a flange 2930, located at the proximal end of the drug delivery device 2910. An injection port 2932 communicates with the internal lumen 2927 for injection of a drug.

Figure 2D:
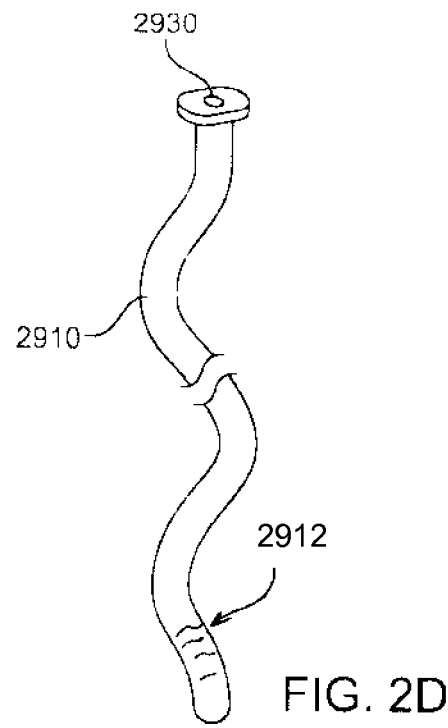
FIG. 2D shows another embodiment of the drug delivery device.

FIG. 2D shows another embodiment of a drug delivery device 2910 that comprises a wicking member without an internal lumen. The wicking member can be formed of a single strand of material or can be formed of a plurality of strands that are interconnected, such as in a twisted, braided, or woven fashion, and through or along which fluid can flow. The wicking member can be a tube that includes an internal lumen that is used to deliver the drug or therapeutic agent directly to the location of the distal end of the delivery device 2910. The wick member(s) do not necessarily include internal lumens, as flow through the wick member can occur via capillary action. In the case of a solid polymer wick, certain surface detents can provide flow lumens between the central body member and the tissue of the suprachoroidal space. The embodiment of FIG. 2D includes a proximal anchor member, such as a flange 2930.

Any of the embodiments of the drug delivery device can include anchoring or retention members, such as fenestrations 2912 on the distal end of the device 2910 in FIG. 2D. The fenestrations 2912 can be located at any location along the length of the device. Moreover, any of the embodiments can include one or more valve members that regulate fluid flow. The valve element can cause fluid to collect in a region of the device and then release the collected fluid such as upon a certain pressure threshold. In this manner, a concentrated amount of drug can be delivered into the eye.

Figure 2E:
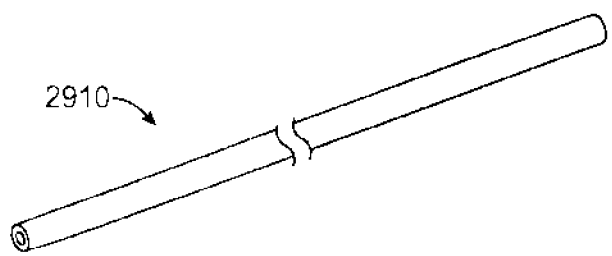
FIG. 2E shows another embodiment of the drug delivery device.
Figure 2F:
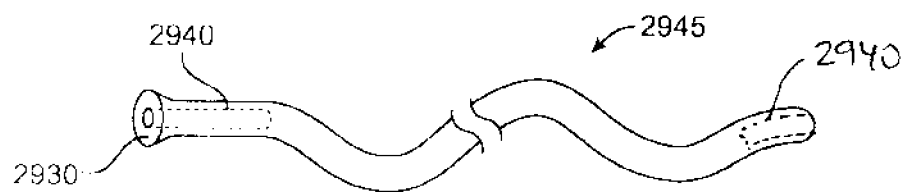
FIG. 2F shows another embodiment of the drug delivery device.

FIG. 2E shows the drug delivery device 2910 as a wicking member without a flange. With reference to FIG. 2F, the drug delivery device 2910 can include a proximal flange 2930 having an injection port that communicates with a drug reservoir 2940. The reservoir can be filled with a drug or other therapeutic agent such that the drug wicks along the length of the drug delivery device. The reservoir can be re-filled with the drug as needed. The flange 2930 can be positioned at the scleral spur when the device is implanted. The reservoir 2940 is positioned adjacent a leaching body 2940 for drug delivery. A reservoir 2940 can also be located at or near the distal end of the device 2910.

In an embodiment, the drug delivery device 2910 is adapted to deliver drops placed on the surface of the eye to suprachoroidal space. This is described further detail below with reference to FIG. 5E. The drug may be delivered to the back regions of the eye, such as regions rearward of the eye equator. One or more drops of a drug or therapeutic agent are placed on the surface of the eye where the drug mixes with the tear film. The tear film directs the drug into an entry port of the drug delivery device 2910. The entry port may be positioned, for example, within the anterior chamber. The drug then flow via the drug delivery device 2910 into the suprachoroidal space and potentially to the back regions of the eye. The drug may mix with aqueous humor as it flows into and along the drug delivery device 2910. In this manner, the drug delivery device 2910 is used to direct drops placed on the eye surface to the back of the eye such as to treat any of a variety of eye diseases.

In another embodiment, a punctal plug is used to deliver a drug to the tear film and into the anterior chamber where the drug intermingles with the aqueous humor. The drug delivery device 29210 then delivers the drug into the suprachoroidal space and possibly to back regions of the eye. Pursuant to such an embodiment, one or more punctal plugs are placed in the eye, such as in the corners of the eye. The punctal plugs can be placed in various regions of the eye, such as in the lower two puncta and/or in the upper puncta. One or more drops of a drug or therapeutic agent are then placed onto the eye such that the drug flows into the anterior chamber via the punctal plugs. The drug then flows into an entry port in the drug delivery device 2910 and flows into the suprachoroidal space via the drug delivery device 2910. International Patent Publication WO 06/014434 to Lazar describes exemplary devices and methods for drug delivery through punctal plugs. That publication is incorporated herein by reference in its entirety.

A wide variety of systemic and ocular conditions such as inflammation, infection, cancerous growth, may be prevented or treated using the drug delivery devices of the present invention. More specifically, ocular conditions such as glaucoma, proliferative vitreoretinopathy, diabetic retinopathy, uveitis, keratitis, cytomegalovirus retinitis, cystoid macular edema, herpes simplex viral and adenoviral infections can be treated or prevented.

Depending on the dose required, and the delivery profile of the agent delivered, it may be advantageous for the drug delivery device to extend from the initial dissection plane at the point of the scleral spur, within the suprachoroidal space to the posterior segment of the eye, or any location therebetween. The geometry of the drug delivery device may assist in the ability to prolong or control various dosing regimes. For example, a longer delivery device may equate to a longer dosing potential, and similarly a larger diameter device may assist with this also. Because the drug delivery device of the present invention completely fills the suprachoroidal space, a "washout" effect may be minimized, thereby also assisting in the dosing. In addition, it may be advantageous to employ a sealant, to seal any communication between the anterior chamber and the newly dissected suprachoroidal space once the drug delivery device is placed. Products such as Tisseal® (Baxter Healthcare, Irvine, Calif.), fibrin glues, or small amounts of cyanoacrylate may be used for this purpose.

Alternatively, if delivery of a therapeutic agent of the present invention is desired in the anterior chamber, or within the sclera, trabecular meshwork, choroid or other structures in proximity to the suprachoroidal space, the entry point at which the delivery device accesses the suprachoroidal space may be varied, such that the distal end of the drug delivery device may be placed in the suprachoroidal space as a means for anchoring the device, and the proximal end (end nearest the outside of the eye) may be placed at the desired delivery location.

Figure 3:
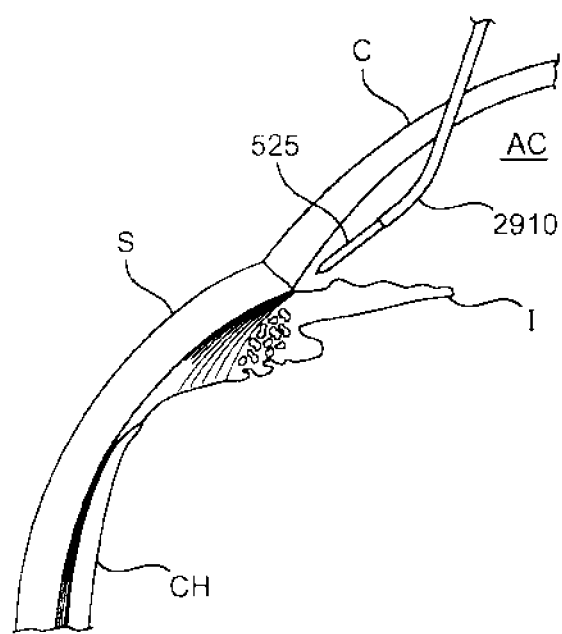
FIG. 3 shows the drug delivery device mounted on a delivery device during deployment of the device.

With reference to FIG. 3, the drug delivery device 2910 can be mounted on an elongate delivery member 525 and can enter the suprachoroidal space at or near the scleral spur. In general, the drug delivery device is implanted using a delivery system by accessing the scleral spur to create a low profile dissection in the tissue plane between the choroid and the sclera. An incision can be formed in the cornea and the drug delivery device is inserted through the incision. The drug delivery device can pass along a pathway through the scleral spur of the eye into the suprachoroidal space. The drug delivery device is then secured in the eye so that it provides communication between a drug delivery inlet and the suprachoroidal space.

Figure 4:
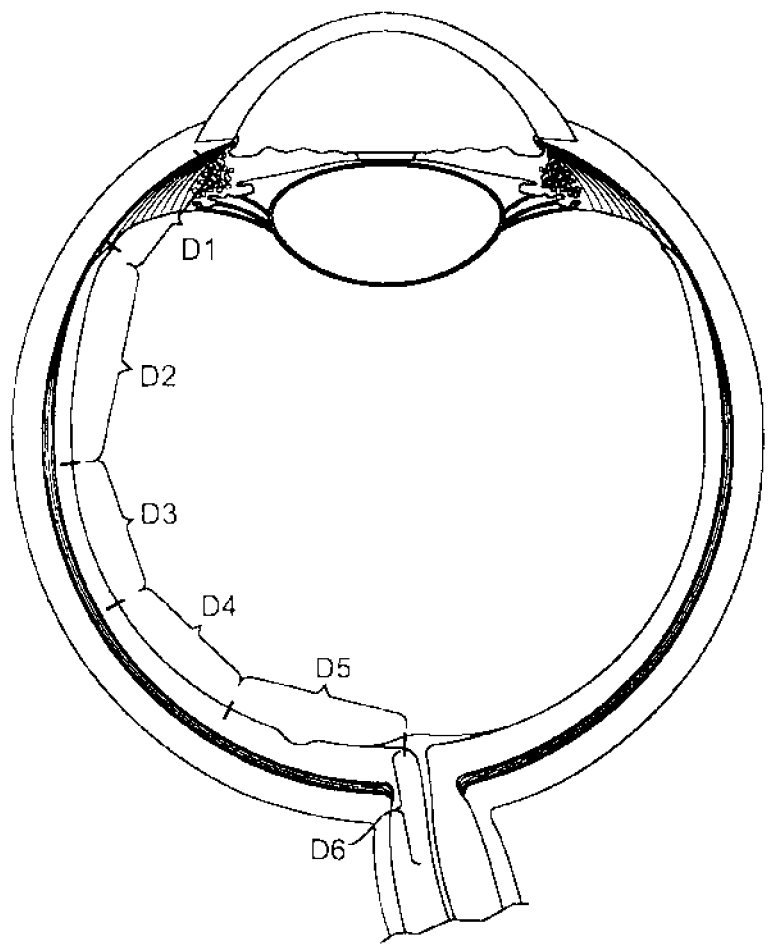
FIG. 4 shows various exemplary regions of the eye where a distal end of the drug delivery device can be located.

The drug delivery device 2910 can be positioned within the suprachoroidal space or can have a length such that the distal end of the drug delivery device is positioned at any of a variety of points along the length of the suprachoroidal space, such as any point from the scleral spur to the back regions of the eye. FIG. 4 shows various regions, D1-D6 where the distal end of the drug delivery device can be located. It should be appreciated that the regions are for purpose of example and do not limit where the distal end can be positioned.

Figure 5A:
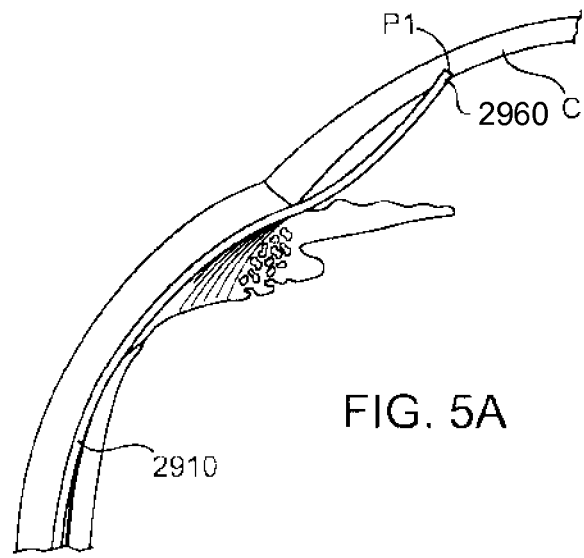
FIGS. 5A-5G show various exemplary regions of the eye where a proximal end of the drug delivery device can be located.
Figure 5B:
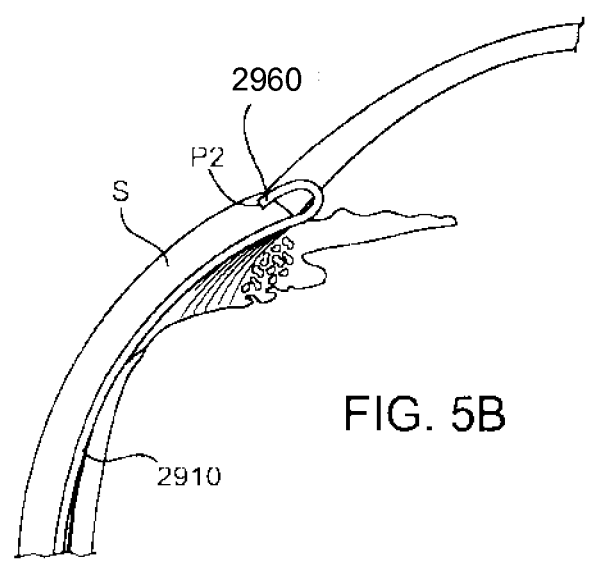
Figure 5C:
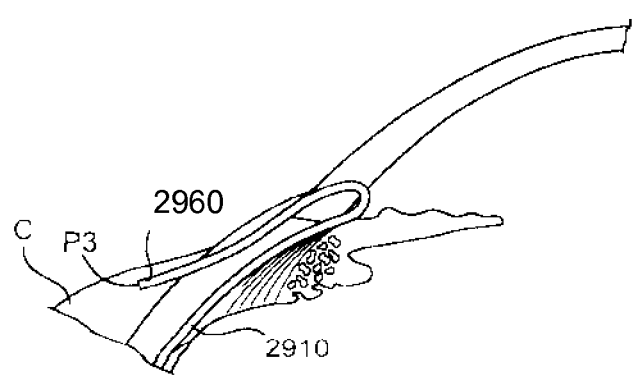
Figure 5D:
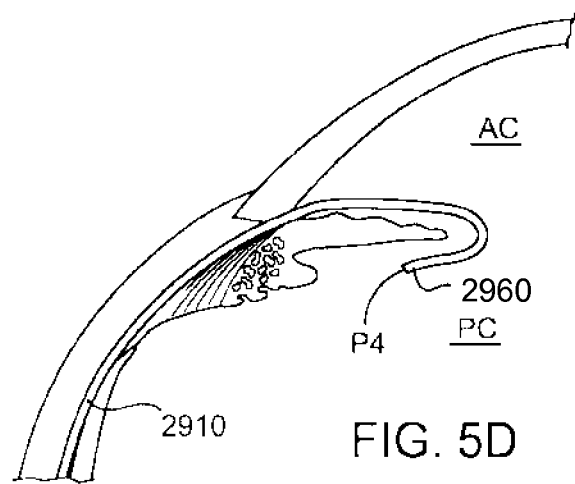
Figure 5E:
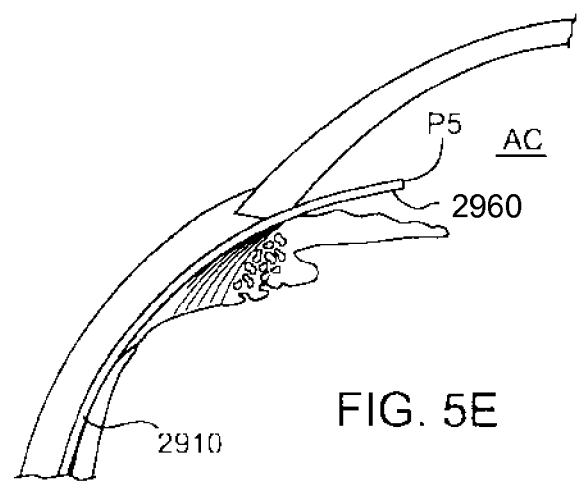
Figure 5F:
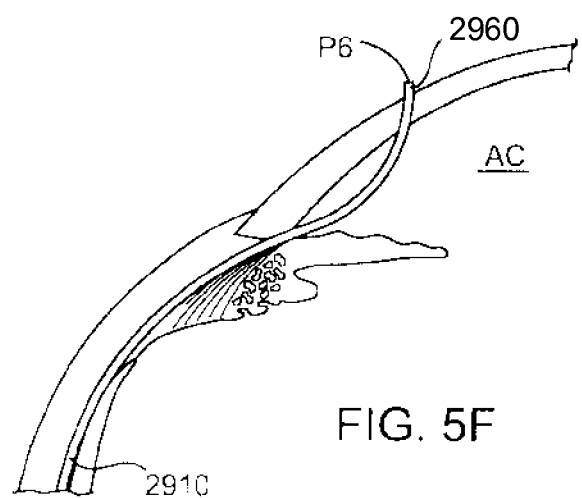

The proximal end of the drug delivery device 2910 can be positioned at various locations relative to the eye, as shown in FIGS. 5A-5F. In FIG. 5A, the proximal end of the drug delivery device 2910 is positioned at a location P1, which is within the cornea C. In FIG. 5B, the proximal end is positioned at a location P2, which is within the sclera S. In FIG. 5C, the proximal end is positioned at a location P3, which is within the conjunctiva C. In FIG. 5D, the proximal end is positioned at a location P4, which is within posterior chamber PC. In FIG. 5E, the proximal end is positioned at a location P5, which is within the anterior chamber AC. In FIG. 5F, the proximal end is positioned at a location P6, which is outside of the eye. Other locations for the proximal end of the drug delivery device are also possible. Moreover, the locations P1-P4 are merely exemplary and are intended to represent regions of the eye rather than exact locations. The drug delivery device can be removed from the eye after drug delivery is complete. The drug delivery device can also be bioabsorbable so that it does not need to be removed.

Figure 5G:
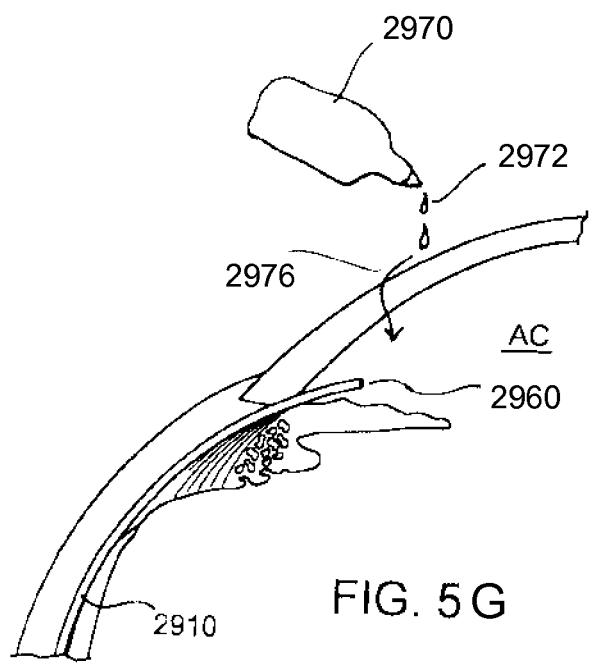

With reference to FIG. 5G, a container, such as a drop bottle 2970, is adapted to deliver one or more drops 2972 of a drug or therapeutic agent onto the surface of the eye. The tear film directs the drug into the anterior chamber, as represented schematically by the arrows 2976 in FIG. 5G. The drug then flows into the entry port 2960 of the drug delivery device 2910, which guides the drug into the suprachoroidal space.

With respect to any of the embodiments of FIG. 5A-5G, the proximal end of the drug delivery device 2910 can include a port 2960 that is adapted to receive a drug. The port 2960 can have various structural configurations and shapes. For example, the port 2960 can be funnel-shaped, flanged, or widened to facilitate entry of the drug into the delivery device. The port 2960 can also be made of a material that is adapted to absorb or otherwise attract the drug.

The following classes of drugs could be delivered using the devices of the present invention: anesthetics, analgesics, cell transport/mobility impending agents such as colchicine, vincristine, cytochalasin B and related compounds; antiglaucoma drugs including beta-blockers such as timolol, betaxolol, atenolol, and prostaglandin analogues such as bimatoprost, travoprost, latanoprost etc; carbonic anhydrase inhibitors such as acetazolamide, methazolamide, dichlorphenamide, diamox; and neuroprotectants such as nimodipine and related compounds. Additional examples include antibiotics such as tetracycline, chlortetracycline, bacitracin, neomycin, polymyxin, gramicidin, oxytetracycline, chloramphenicol, gentamycin, and erythromycin; antibacterials such as sulfonamides, sulfacetamide, sulfamethizole and sulfisoxazole; anti-fungal agents such as fluconazole, nitrofurazone, amphotericine B, ketoconazole, and related compounds; anti-viral agents such as trifluorothymidine, acyclovir, ganciclovir, DDI, AZT, foscamet, vidarabine, trifluorouridine, idoxuridine, ribavirin, protease inhibitors and anti-cytomegalovirus agents; antiallergenics such as methapyriline; chlorpheniramine, pyrilamine and prophenpyridamine; anti-inflammatories such as hydrocortisone, dexamethasone, fluocinolone, prednisone, prednisolone, methylprednisolone, fluorometholone, betamethasone and triamcinolone; decongestants such as phenylephrine, naphazoline, and tetrahydrazoline; miotics and anti-cholinesterases such as pilocarpine, carbachol, di-isopropyl fluorophosphate, phospholine iodine, and demecarium bromide; mydriatics such as atropine sulfate, cyclopentolate, homatropine, scopolamine, tropicamide, eucatropine; sympathomimetics such as epinephrine and vasoconstrictors and vasodilators; Ranibizumab, Bevacizamab, and Triamcinolone.

Non-steroidal anti-inflammatories (NSAIDs) may also be delivered, such as cyclooxygenase-1 (COX-1) inhibitors (e.g., acetylsalicylic acid, for example ASPIRIN® from Bayer AG, Leverkusen, Germany; ibuprofen, for example ADVIL® from Wyeth, Collegeville, Pa.; indomethacin; mefenamic acid), COX-2 inhibitors (CELEBREX® from Pharmacia Corp., Peapack, N.J.; COX-1 inhibitors), including a prodrug Nepafenac®; immunosuppressive agents, for example Sirolimus (RAPAMUNE®, from Wyeth, Collegeville, Pa.), or matrix metalloproteinase (MMP) inhibitors (e.g., tetracycline and tetracycline derivatives) that act early within the pathways of an inflammatory response. Anticlotting agents such as heparin, antifibrinogen, fibrinolysin, anti clotting activase, etc., can also be delivered.

Antidiabetic agents that may be delivered using the present devices include acetohexamide, chlorpropamide, glipizide, glyburide, tolazamide, tolbutamide, insulin, aldose reductase inhibitors, etc. Some examples of anti-cancer agents include 5-fluorouracil, adriamycin, asparaginase, azacitidine, azathioprine, bleomycin, busulfan, carboplatin, carmustine, chlorambucil, cisplatin, cyclophosphamide, cyclosporine, cytarabine, dacarbazine, dactinomycin, daunorubicin, doxorubicin, estramustine, etoposide, etretinate, filgrastin, floxuridine, fludarabine, fluorouracil, fluoxymesterone, flutamide, goserelin, hydroxyurea, ifosfamide, leuprolide, levamisole, lomustine, nitrogen mustard, melphalan, mercaptopurine, methotrexate, mitomycin, mitotane, pentostatin, pipobroman, plicamycin, procarbazine, sargramostin, streptozocin, tamoxifen, taxol, teniposide, thioguanine, uracil mustard, vinblastine, vincristine and vindesine.

Hormones, peptides, nucleic acids, saccharides, lipids, glycolipids, glycoproteins, and other macromolecules can be delivered using the present devices. Examples include: endocrine hormones such as pituitary, insulin, insulin-related growth factor, thyroid, growth hormones; heat shock proteins; immunological response modifiers such as muramyl dipeptide, cyclosporine, interferons (including a, [3, and y interferons), interleukin-2, cytokines, FK506 (an epoxy-pyrido-oxaazcyclotricosine-tetrone, also known as Tacrolimus), tumor necrosis factor, pentostatin, thymopentin, transforming factor beta2, erythropoetin; antineogenesis proteins (e.g., anit VEGF, Interfurons), among others and anticlotting agents including anticlotting activase. Further examples of macromolecules that can be delivered include monoclonal antibodies, brain nerve growth factor (BNGF), celiary nerve growth factor (CNGF), vascular endothelial growth factor (VEGF), and monoclonal antibodies directed against such growth factors. Additional examples of immunomodulators include tumor necrosis factor inhibitors such as thalidomide.

In addition, nucleic acids can also be delivered wherein the nucleic acid may be expressed to produce a protein that may have a variety of pharmacological, physiological or immunological activities. Thus, the above list of drugs is not meant to be exhaustive. A wide variety of drugs or agents may be used in the present invention, without restriction on molecular weight, etc.

Additional examples of beneficial drugs that may be employed in the present invention and the specific conditions to be treated or prevented are disclosed in Remington, supra; The Pharmacological Basis of Therapeutics, by Goodman and Gilman, 19th edition, published by the MacMillan Company, London; and The Merck Index, 13th Edition, 1998, published by Merck & Co., Rahway, N.J., and U.S. Pat. No. 6,331,313 to Wong, which is previously expressly incorporated herein by reference, including the above text.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

What is claimed is:

1. A method of delivering drug into the eye, comprising:
   inserting an elongate member through a cornea and through an anterior chamber of the eye, wherein the elongate member has a first end, a second end, and an internal lumen with a first opening near the first end and a second opening near the second end;
   positioning the elongate member in the eye such that the first end is in the anterior chamber, the second end is in communication with a suprachoroidal space of the eye, and at least a portion of the elongate member between the first end and the second end is positioned between the sclera and a ciliary body of the eye;
   placing a treatment medium onto an outer surface of the eye; and
   causing the treatment medium to flow into the internal lumen of the elongate member and into the suprachoroidal space through the internal lumen of the elongate member.

2. A method as in claim 1, wherein the treatment medium flows into the anterior chamber via tear film.

3. A method as in claim 1, wherein the elongate member is implanted in the eye such that the second end is positioned in an anterior portion of the eye.

4. A method as in claim 1, wherein the elongate member is implanted in the eye such that the second end is positioned between a sclera and a choroid of the eye.

5. A method as in claim 1, wherein the elongate member is implanted in the eye such that the second end is positioned between a sclera and a ciliary body of the eye.

6. A method as in claim 1, wherein placing a treatment medium onto an outer surface of the eye comprises placing a drop of treatment medium onto an outer surface of the eye.

7. A method as in claim 1, wherein the elongate member is implanted in the eye such that the elongate member is positioned adjacent a scleral spur of the eye.

8. A method as in claim 1, wherein the elongate member is implanted in the eye such that no portion of the elongate member between the first end and the second end is positioned inside the sclera.

\* \* \* \* \*